United States Patent [19]

Wang

[11] 4,315,010
[45] Feb. 9, 1982

[54] GLAUCINE PHOSPHATE SALTS

[75] Inventor: Samuel S. M. Wang, Indianapolis, Ind.

[73] Assignee: The Dow Chemical Company, Midland, Mich.

[21] Appl. No.: 57,483

[22] Filed: Jul. 13, 1979

Related U.S. Application Data

[63] Continuation-in-part of Ser. No. 935,221, Aug. 21, 1978, abandoned.

[51] Int. Cl.$^3$ .................. A61K 31/485; C07D 215/20; C07D 215/22
[52] U.S. Cl. ..................................... 424/260; 546/75
[58] Field of Search .................. 424/260; 260/286 R; 546/75

[56] References Cited

FOREIGN PATENT DOCUMENTS 866079  4/1978  Belgium.

OTHER PUBLICATIONS

Ishiwata et al., Chem. Pharm. Bull., vol. 18, pp. 1219–1223, 1224–1227 (1970).
Donev, Farmatsiya (Sofia), 12 (4), 17–21 (1962) 14 (2) 49–54 (1964).
Chem. Abst., vol. 71, 74043 D (1969).
Chem. Abst., vol. 66, 31978 S (1967).
Chem. Abst., vol. 61, 9928 G (1964).
Chem. Abst., vol. 58, 4941 H (1963).

*Primary Examiner*—Stanley J. Friedman

[57] ABSTRACT

Novel phosphate salts of 1 and d,l-glaucine are prepared by reacting 1 or d,l-glaucine base with phosphoric acid. The glaucine salts have potent analgesic and antitussive properties, excellent flavor characteristics and stability properties. Pharmaceutical compositions, and methods of using the same are also described.

17 Claims, No Drawings

GLAUCINE PHOSPHATE SALTS

CROSS REFERENCE TO RELATED APPLICATION

This is a continuation-in-part of my copending application, Ser. No. 935,221, filed Aug. 21, 1978 and now abandoned.

BACKGROUND OF THE INVENTION

Dextro-rotary glaucine or d-glaucine hydrobromide has been used as an antitussive agent. D-glaucine can be isolated from the yellow poppy. The racemate, d,l-glaucine can be synthesized from papaverine, following the procedure of Frank and Tietze, Angewandte Chemie (1967) pp 815–6, or Helm, Belgian Pat. No. 866,079, and the racemate can be resolved with d-tartaric acid as disclosed by the above mentioned Helm Belgian patent. A variety of other preparative procedures are also known. Cham and Maitland, J. Org. Chem. J. Chem. Soc. (C) 1966, 753; and Cava, et al. J. Org. Chem. 35, 175 (1970). Separation of the isomers has been carried out by conventional procedures, such as using d- or l-tartaric acid to form the d- or l-bitartrate salts and separating the salts by fractional crystallization.

Glaucine has the structure

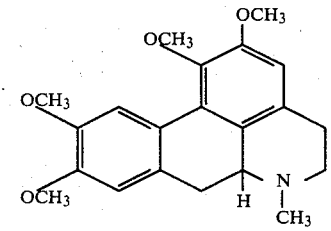

and is thus structurally related to other plant alkaloids such as codeine and aporphine.

Codeine, and the related compounds such as hydrocodone, dihydrocodeine and dextromethorphan are well known as antitussive agents. Merck Index, Ninth Ed., Merck & Co., Rahway, N.J. (1976) monographs Nos. 2420–24, 3148, 4672, and 7908. Although these compounds, particularly codeine, are also well known to have a high potential for habituation or addiction, they are widely used, and codeine remains the most potent and widely used antitussive agents despite its abuse potential and other side effects. Codeine, hydrocodone, and dihydrocodeine have also been used as narcotic analgesics.

Antitussive agents are usually administered orally, most typically in the form of a liquid formulation such as an elixir, suspension or syrup, or in a solid lozenge or cough drop which is held in the mouth until it dissolves. In both cases the unpleasant bitter flavor of the alkaloid is known disadvantage of such agents. Various formulations have been developed to mask the unpleasant taste and after taste of codeine, dihydrocodeine and dextromethorphan, with varying degrees of success. None of these techniques have been completely successful. Glaucine, like codeine, has an unpleasant bitter taste.

SUMMARY OF THE INVENTION

This invention is directed to the phosphate salts of l-glaucine, d,l-glaucine and mixtures of l- and d,l-glaucine, to pharmaceutical compositions containing said salts and to methods for using them as antitussive agents.

It has now been found that l-and d,l-glaucine phosphate salts have antitussive properties that are unexpectedly superior to the d-glaucine, and that d,l and l-glaucine phosphate salts have desirable solubility and high stability properties, unexpected flavor and palatability properties, analgesic activity, and low addictive potential.

The novel glaucine phosphate salts include the phosphates of the l-glaucine mixed with up to an equimolar amount of d-glaucine. Since a mixture of equimolar amounts of the levo- and dextro-rotary isomers is a racemic d,l-mixture, the mixed enantiomers of the invention can be referred to as the racemate or a mixture of the racemate with the l-enantiomer, i.e., as d,l-glaucine or a mixture of l-and d,l-glaucine.

The novel phosphate salts of the invention are crystalline solids which are prepared by reacting l-glaucine or d,l-glaucine (or mixtures thereof) in the form of the base, with phosphoric acid under conditions adapted to the formation of phosphate salts of organic bases. The crystalline solid salts include from about 0.3 to 0.4 to about 0.6 or 0.7 molar proportion of excess phosphoric acid, typically one mole of glaucine base to about 1.4 to 1.6 moles of phosphoric acid. The predominant crystalline phosphate salt, readily obtained using excess phosphoric acid, includes about 1.4 to 1.6 and usually about 1.5 molecular proportions of phosphoric acid per molecular proportion of 1 or d,l-glaucine. The molecular porportions of glaucine and phosphoric acid can be determined by conventional procedures such as elemental analysis, or by X-ray crystallography and crystal density measurements. This salt can be referred to as glaucine phosphate (2:3), or (glaucine)$_2$.3H$_3$PO$_4$, or glaucine.1½H$_3$PO$_4$, for example.

The l- and d,l-glaucine phosphate salts melt in the range from about 240°–254° C. and have useful solubility in water, and are less soluble in organic solvents such as methylene chloride, acetone and diethyl ether. They are acidic in solution and generally have a pH in water solution (0.5 grams/100 ml) of about 2.4–2.6. The exact melting point of particular preparations can vary depending on the preparative and purification procedures used, indicating that factors such as water of hydration or crystalline solvate formation with the reaction medium or with recrystallization solvents may be involved.

Depending on the amounts of reactants employed, the glaucine phosphate salt can contain a minor amount of a second glaucine phosphate, believed to be diglaucine phosphate, detectable by a differential scanning calorimetry peak at about 219°–221° C., although the elemental analysis confirms the (2:3) structure. This peak can be removed by treating the product with additional phosphoric acid, to obtain the glaucine phosphate (2:3) salt free of the lower melting impurity. The salts can also be obtained in association with unreacted phosphoric acid, when large excesses of phosphoric acid are employed. Excess associated phosphoric acid can be removed by conventional techniques such as filtration, or partial neutralization. When excess l- or d,l-glaucine is employed, the salts can also be obtained in association with unreacted glaucine, depending on the reaction conditions and solvent employed. Unreacted glaucine can be removed by conventional purification techniques such as recrystallization and washing, or converted to the phosphate salt with additional phosphoric acid.

The compounds can be readily prepared by reacting the free glaucine base with phosphoric acid. The reaction proceeds readily in the presence of an inert organic sovlent, such as acetone, ethanol, chloroform, methylene chloride, methanol, or diethyl ether, or ethyl acetate. The phosphate salt typically forms as a precipitate, which can be recovered by conventional techniques such as filtration or decantation and purified by conventional steps such as recrystallization and washing.

The reaction is typically carried out by dissolving the free base glaucine in the inert organic solvent at a temperature from ambient temperature to the boiling point of the mixture, and mixing the solution with an excess of phosphoric acid. PHosphoric acid is employed in from about 0.5 to about 1 to 2 to 3 fold molar excess or more. Use of equimolar amounts or excess glaucine reactant can result in obtention of a mixture of the glaucine phosphate (2:3) salt with impurities such as unreacted or partially reacted glaucine base. Such products can be reacted with additional phosphoric acid to convert the impurities to glaucine phosphate (2:3).

When using excess phosphoric acid, so as to obtain the glaucine phosphate (2:3) salt in relatively pure form or a solid phosphate associated with excess phosphoric acid, any excess phosphoric acid content can be reduced by partial neutralization followed by recrystallization. In such procedure, the solid salt is first titrated to determine the molar amount of phosphate in excess over the molar amount of glaucine. The solid salt can then be mixed with alcoholic alkali metal hydroxide base, such as sodium or potassium hydroxide in methanol or ethanol, using an amount of a alkali metal hydroxide sufficient to neutralize the excess phosphoric acid. The glaucine phosphate (2:3) salt can then be purified by conventional recrystallization, for example, with ethanol. Partial neutralization is generally unnecessary to obtain a useful salt in crystalline form. Preferably, the product is digested by heating under reflux in ethanol for four to eight hours, before recrystallization and drying.

When the salts are in solution, the ratio of glaucine to phosphoric acid can be increased by conventional procedures such as partial titration to reduce the level of phosphoric acid. Such procedures can produce mixtures of the glaucine base and the glaucine phosphate salt, and can lead to precipitation of the free base. Addition of excess phosphoric acid substantially beyond the (2:3) molar ratio in the salt generally results in precipitation of the glaucine phosphate salt.

Mixtures of the d,l- and l-glaucine phosphate salts and the salts, whether or not associated or complexed with additional phosphoric acid or containing minor amounts of unreacted or partially reacted glaucine are all useful as antitussive agents and analgesic agents, with similar desirable properties. For convenience it is generally preferred to use a single phosphate salt, such as the d,l-glaucine phosphate or l-glaucine phosphate. The preferred salt is the salt having 1.5 molar proportions of phosphoric acid per molar proportion of d,l-glaucine.

The glaucine phosphate salts are highly effective, orally active antitussive agents and also have analgesic activity when administered orally, combined with surprising palatability and desirable stability and solubility, and a useful freedom from undesired side effects, such as addictive properties. They can be administered at dosages of from about 0.1 to about 40 milligrams or more per kilograms (mg/kg) for antitussive effect, and from about 0.1 to about 60 mg/kg for analgesic use, preferably by oral administration. They are also active parenterally as antitussives and analgesics, by intraperitioneal injection, for example.

In practicing the method of the invention, an antitussive amount of one or more of the glaucine phosphates, is administered internally to an animal, typically a mammal in need thereof. Administration can be carried out either by a parenteral route, such as by intravenous, intraperitoneal, or intramusuclar injection; or by introduction into the gastrointestinal tract via oral or rectal administration, for example, or by oral administration of a glaucine phosphate solution in the form of a throat spray; for example.

The antitussive amount of the compound, that is, the amount of the glaucine phosphate sufficient to inhibit or alleviate coughing depends on various factors such as the size, type and age of the animal to be treated, the particular salt or mixture of salts employed, the route and frequency of administration, the severity of cough (if any) and the causative agent involved, and the time of administration. Similar considerations apply to selection of an analgesic dose for administration to animals. The glaucine phosphate salts are generally effective at low dosages when administered orally as compared to parenteral dosages. For example, in antitussive evaluations in which codeine phosphate has an $ED_{50}$ of 10.9 mg/kg by intraperitoneal injection and an oral $ED_{50}$ of 86.6 mg/kg, the oral and intraperitoneal $ED_{50}$'s obtained with $(d,l$-glaucine$)_2.3H_3PO_4$ are quite similar, 17.8 and 17.3 mg/kg. In particular cases, the dosage to be administered can be ascertained by conventional range finding techniques, for example, by observing the antitussive activity produced at different dosage rates.

Good antitussive results can be obtained when the salts are administered orally at dosage rates from about 0.1 to about 0.2, to about 0.5 to about 1 to about 10 to about 20 to 25 to 30 to 40 to about 80 milligrams of glaucine salt compound per kilogram of animal body weight and at rates of 0.1 to 40 mg/kg by intraperitoneal injection. It is generally desirable to administer individual dosages at the lowest amount which provides the desired cough suppression from consonant with a convenient dosing schedule. Oral administration is the route generally preferred for administration of antitussive agents. The glaucine phosphates of the invention thus combine high oral antitussive potency with palatability.

Dosage units adaptable to oral administration such as tablets, capsules, lozenges, elixirs, syrups and the like are preferred and the active glaucine phosphate compound can be formulated in conventional timed release capsule or tablet formulations.

In using the compounds of the invention, the active glaucine phosphate ingredient is preferably incorporated in a composition comprising a pharmaceutical carrier and from about 0.001 to about 95 percent by weight of the glaucine phosphate salt compound or a pharmacologically-acceptable salt thereof. The term "pharmaceutical carrier" refers to known pharmaceutical excipients useful in formulating pharmacologically-active compounds for internal administration to animals, and which are substantially non-toxic and non-sensitizing under conditions of use. The compositions can be prepared by known techniques for the preparation of tablets, capsules, cough drops, lozenges, troches, suppositories, solutions, elixirs, syrups, emulsions, dispersions, wettable and effervescent powders, sterile injectable compositions, and can contain suitable excipients known to be useful in the preparation of the particular type of composition desired. As with phosphates generally, liquid compositions should generally be substantially free of cations which form highly insoluble phosphate salts, to avoid undesired salt precipitation.

The compounds may be administered in conjunction with other active ingredients or other antitussive or analgesic agents. Other active ingredients can include, for example, antihistamines, decongestants, expectorants, mucolytic agents, bronchodilators and antibacterial agents or local anesthetics. Combinations of this type are generally useful for treating coughing or pain in combination with other symptoms.

Particularly desirable compositions are those prepared in the form of dosage units, such as solid forms, including troches, lozenges, tablets, capsules, or measured volumes of liquid compositions, containing from about 0.1 milligram to about 20 to 30 to 40 milligrams of the glaucine salt per unit, for antitussive use and from about 0.1 milligram to about 30 to about 60 milligrams for analgesic use.

EXAMPLE 1

Preparation of d,l-Glaucine Phosphate

A. 43.5 Grams (0.1 mole) of glaucine hydrobromide was suspended in 200 milliliters of deionized water in a separated funnel. 50 Milliliters of aqueous 10 percent sodium hydroxide was added, and the resulting mixture was extracted twice with chloroform using 100 milliliters of chloroform for each extraction. The combined chloroform extracts were dried over anhydrous sodium sulfate, filtered and concentrated to dryness under reduced pressure. The resulting white solid d,l-glaucine base was obtained as a residue, melting at 139° C. (Yield 96%.) When desired it can be purified further by recrystallization from ethyl acetate.

B. 3.6 Grams (0.01 mole) of d-l-glaucine base was dissolved in 150 milliliters of Alcohol USP (95 percent ethanol, 5 percent water), with warming to a temperature of 60° C. A solution of 2.0 grams (0.022 mole) of phosphoric acid (85 percent phosphoric acid in water) dispersed in 100 milliliters of Alcohol USP (95 percent ethanol, 5 percent water) was added slowly, with stirring, over a period of about twenty minutes. The d,l-glaucine phosphate product began to appear as a precipitate during the phosphoric acid solution. The product was separated by filtration, and found to melt at 240° C. with decomposition. The white crystalline solid product was recrystallized by mixing with 80 percent ethanol in water; heating under reflux and cooling to ambient temperature. The recrystallized product was then taken up and stirred in a mixture of diethyl ether (3 parts) to one part ethanol, separated by filtration, dried and found to melt at 247° C. with decomposition. (Yield 94.3%.) C, H, N (calculated) for $C_{21}H_{25}NO_4.1\frac{1}{2}H_3PO_4$: 50.2, 5.91, 2.79; (found): 50.29, 6.03, 2.93.

The elemental analysis is thus consistent with the structure $(d,l-glaucine)_2.3H_3PO_4$. (The theoretical C, H, N contents calculated for a 1:1 glaucine phosphate $(C_{21}H_{25}NO_4.H_3PO_4)$ are 55.63, 6.22, and 3.09.)

By differential scanning calorimetry the product appears to be at least 95 percent pure, with a single large peak at 247° C., and with about 5 percent or less as a single small peak believed to be di-d,l-glaucine phosphate at 221° C. The $(d,l-glaucine)_2.3H_3PO_4$ crystals are discrete, well-formed white crystals of rod-like to needle-like shape.

C. In a similar procedure 2 grams of l-glaucine hydrobromide was suspended in water, 5 milliliters of aqueous 10 percent sodium hydroxide was added, and the mixture was extracted with two 50 milliliter portions of chloroform. The extracts were dried, filtered and evaporated to dryness. The resulting l-glaucine base was reacted with 0.25 mole phosphoric acid in a procedure similar to that in Example 1B. The crystalline product was separated, dissolved in 5 milliliters of 95 percent ethanol and reprecipitated by addition of diethyl ether, and recrystallized a second time from ethanol. The white crystalline $(l-glaucine)_2.3H_3PO_4$-[l-glaucine phosphate (2:3)] product was found to melt at 242.0° C., with decomposition. In a similar procedure with an additional recrystallization from ethanol the product was found to melt at 253° C.

D. In a similar procedure 56.8 grams of d,l-glaucine in 250 milliliters Alcohol USP was reacted with 32 grams of 85 percent phosphoric acid in 500 milliliters Alcohol USP, by adding the glaucine base solution to the phosphoric acid solution. The product showed two peaks by differential scanning calorimetry, one at about 245° C. and a smaller peak at about 219° C. (believed to be di-d,l-glaucine phosphate). The $(d,l-glaucine)_2.3H_3PO_4$ product was dried overnight at 120° C. and found by elemental analysis to have C, H, N, O contents of 50.66, 6.06, 3.23 and 30.09 percent and a phosphorus content (P) of 10.07. Theoretical C, H, N, O and P calculated for $C_{21}H_{25}NO_4.1\frac{1}{2}H_3PO_4$: 50.20, 5.91, 2.79, 31.85 and 9.25.

E. In a similar procedure, a d,l-glaucine phosphate was prepared. C, H, N, P: calculated for $C_{21}H_{25}NO_4.1.4 H_3PO_4$: 51.15, 5.97, 2.84, 8.8; C, H, N found: 50.80, 6.00, 2.95 (average of four replications) and P 8.22.

F. A sample of the d,l-glaucine phosphate (2:3) salt of Example 1.D, melting at 245.2° C., was washed thoroughly with a mixture of 3 parts diethylether and one part ethanol, dried and found to melt at 250.7° C. A mixture of the washed and unwashed crystals was found to melt at 242.2° C., indicating the presence of different crystalling solvates in the two glaucine phosphate preparations.

G. 1 Gram (0.0028 mole) of d,l-glaucine was dissolved in 30 milliliters of distilled acetone. 0.3 Gram (0.003 mole) of 85 percent phosphoric acid was added. The resulting white precipitate was removed by filtration, washed with 20 ml of dry acetone, dried in air then dried at 50°–55° C. under vacuum overnight. The glaucine phosphate product (1.0 gram yield) was found to melt at 240°–243° C. C, H, N: found: 51.2, 6.07, 2.96; calculated for $C_{21}H_{25}NO_4.1\frac{1}{2}H_3PO_4$: 50.2, 5.91, 2.79. In a similar operation using 0.6 gram d,l-glaucine in 20 ml of acetone and 0.4 grams phosphoric acid, the washed, air dried product was dried under vacuum at 60° for about 2½ days. The glaucine phosphate was found to melt at 240°–242° C. C, H, N: found: 49.3, 5.91, 2.76; C, H, N calculated for $C_{21}H_{25}NO_4.1.6-H_3PO_4$: 49.24, 5.86, 2.73.

H. 2.5971 Kilograms (5.95 mole) of d,l-glaucine hydrobromide, 10.0 liters of deionized water, and 3.5 liters of methylene chloride were mixed. The mixture was stirred rapidly, and 500 milliliters of 50 percent sodium hydroxide were slowly added. The sodium hydroxide was washed in with 100 milliliters of deionized water. After the addition was complete, the mixture was stirred for 15 minutes. The stirrer was then stopped and the mixture allowed to stand for 10 minutes to permit the layers to separate. The methylene chloride layer was drained off and stored. The aqueous layer was mixed with 3.5 liters of methylene chloride, and the mixture stirred rapidly for 15 minutes. The mixture was allowed to stand for 10 minutes to permit the layers to separate. The methylene chloride layer was drained off. An additional 200 milliliters of methylene chloride was added to the aqueous layer. The methylene chloride layer was drained off. The methylene chloride layers were combined and mixed with 3 liters of deionized water.

The resulting mixture was stirred rapidly for 15 minutes then allowed to stand for 15 minutes to permit the layers to separate. The methylene chloride layer was drained off and stored. This methylene chloride solution of d,l-glaucine base was then added to a well-stirred solution of 1.4235 kilograms (12.35 mole) of 85 percent phosphoric acid in 9.8 liters of toluene denatured, absolute ethanol. A heavy, white slurry formed. The slurry was stirred for 15 minutes, and then allowed to stand, under nitrogen, for about 14–16 hours. The stirrer was then started, and the slurry was slowly drained into 3 liter, sintered glass funnels. The solid which resulted was placed in large glass drying dishes and air dried, then vacuum dried at 50°–65° C. to give 2.902 kilograms (97.1 percent yield) of d,l-glaucine phosphate.

A 22 liter flask was charged with 1.500 kilograms of the d,l-glaucine phosphate and 15 liters of 80 percent toluene-denatured, absolute ethanol (20 percent water). The mixture was stirred and heated to reflux (78° C.) under nitrogen. The slurry was held at reflux for 5–6 hours, then allowed to cool to 22°–25° C. The slurry was then slowly drained into 3 liter sintered glass funnels. The resulting solid was then air-dried. The solid was thoroughly washed with 3 liters of toluene denatured, absolute ethanol and air-dried again. The solid was then vacuum dried at 50°–65° C. to give 1.375 kilogram (91.7 percent recovery) of d,l-glaucine phosphate.

By differential scanning calorimetry, the product showed a single peak, with a melting point of 253° C. C, H, N, found: 50.2, 5.97, 2.67; C, H, N calculated for $C_{21}H_{25}NO_4.1.5H_3PO_4$: 50.2, 5.91, 2.79.

I. L-Glaucine phosphate, prepared as described above, was recrystalized three times from ethanol to obtain the purified salt in fine, powder-like crystals. C, H, N, Found: 50.20, 5.91, 2.73; C, H, N, Calculated for $C_{21}H_{25}NO_4—.1.5H_3PO_4$: 50.2, 5.91, 2.79.

J. Crystal density of d,l-glaucine phosphate was measured by suspending at least four crystals of d,l-glaucine.$1.5H_3PO_4$ in a solution mixture of benzene and carbon tetrachloride; adjusting the ratio of benzene and carbon tetrachloride to equal density with the suspended crystals; and measuring density of the solution mixture which produced an equal-density suspension using a pynchnometer. The crystal density thus observed was 1.460 grams per cubic centimeter.

Unit cell constants for the d,l-glaucine.$1.5H_3PO_3$ crystals were measured by single crystal X-ray crystallography. The cell dimensions were found to be $a = 89.854$ Angrstom units; $b = 8.565$ Angstrom units and $c = 23.830$ Angstrom units, the crystals being monoclinic with a $\beta$ angle of 93.7°. Theoretical densities were calculated using as the smallest apparent cell volume $V = 1/8$ abc sin $\beta = 2.286$ cubic Angstrom units $(2.286 \times 10^{-21}$ cubic centimeters) and Z equal to four molecules per small cell volume. For a (1:1) glaucine phosphate the calculated theoretical density $$\frac{\text{Gram Molecular Weight}}{\text{Avogadro Number}} \times \frac{Z}{V}$$

was 1.319 grams/cm³. For a (1:2) salt, glaucine diphosphate, the theoretical density was 1.602 grams/cm³. For a (2:1) salt, diglaucine monophosphate, the theoretical density is greater than 2.3 grams/cm³. For d,l-glaucine.$1.5H_3PO_4$ the theoretical calculated crystal density was 1.460 grams/cm³, which corresponds to the observed crystal density.

EXAMPLE 2

Separate groups of guinea pigs were orally administered various doses of a test compound, or distilled water for a control group. One hour after oral dosing, the guinea pigs were exposed to a 5 percent aerosol of citric acid for a 10 minute test period. The number of cough responses produced during the last five minutes of exposure to the citric acid aerosol was recorded and the dosage effect to suppress coughing in 50 percent of the guinea pigs ($ED_{50}$) was calculated. An antitussive effect was recorded for a guinea pig when its total number of coughs during the 5 minute test period were at least two standard deviation units below the mean number of coughs per guinea pig in the control group. In these operations, codeine phosphate was found to have an oral $ED_{50}$ of 86.6; d-glaucine hydrobromide an $ED_{50}$ of 89.0; d-glaucine phosphate an $ED_{50}$ of 170.1; d,l-glaucine phosphate [d-l-glaucine)$_2$.3($H_3PO_4$)] an $ED_{50}$ of 17.8; and l-glaucine phosphate [(l-glaucine)$_2$.3($H_3PO_4$)] an $ED_{50}$ of 10.9 milligrams per kilogram.

The 95 percent confidence limits of the $ED_{50}$'s determined for codeine phosphate, the d,l-glaucine phosphate and the 1-glaucine phosphate were 52.3–232.6; 6.0–53.1; and 0.4–33.8, respectively. The data indicate that the glaucine phosphates are approximately 4 to 8 times as potent as codeine in this test.

EXAMPLE 3

In an operation similar to that of Example 2, test compounds were administered to guinea pigs by intraperitoneal injection, with one group of guinea pigs receiving distilled water as a control. $ED_{50}$'s were calculated for antitussive activity in the critic acid aerosol test as described in Example 2. Codeine phosphate was found to have an $ED_{50}$ of 10.9 mg/kg; d-glaucine hydrobromide an $ED_{50}$ of 10.0 mg/kg; and d,l-glaucine phosphate [(d,l-glaucine)$_2$.3($H_3PO_4$)] an $ED_{50}$ of 17.3 mg/kg.

EXAMPLE 4

A cough syrup vehicle formulation was prepared containing the following pharmaceutically-acceptable excipients:

| Excipient | Amount |
|---|---|
| Sugar (cane) | 1600 grams |
| Sorbitol solution USP | 600 grams |
| Ethanol (Alcohol USP) | 21 grams |
| Water | q.s. to 4 liters total |

The solubility of d,l-glaucine hydrobromide in this cough syrup vehicle was found to be 0.3 percent, or about 15 milligrams in a 5 milliliter dosage unit. The solubility of d,l-glaucine phosphate was found to be 1 percent, or about 50 milligrams per 5 milliliter dosage unit.

EXAMPLE 5

Stability of d,l-glaucine phosphate was examined in the syrup vehicle of Example 4. After one month at ambient temperature, 40° C. and 55° C., respectively, syrup formulated to contain 0.6 percent d,l-glaucine phosphate was found to retain 101.3, 100.0 and 98.4 percent, respectively, of the original glaucine concentration.

Syrups containing codeine phosphate, 0.2 percent contained 97.5, 104.5 or 100 percent, respectively, after one month at ambient temperature, 40° C. or 55° C. Syrups containing d,l-glaucine hydrobromide, 0.2 percent, resulted in assays of 99, 96 and 89.5 percent, respectively, after one month at ambient temperature, 40° C. and 55° C. After three months, the percentage amount of antitussive agent remaining was as shown below.

| Compound | Percentage Remaining after 3 months at, | | |
|---|---|---|---|
| | Ambient | 40° C. | 50° C. |
| d,l-Glaucine Phosphate (2:3) | 101.6 | 101.1 | 98.7 |
| Codeine Phosphate | 101.3 | 101.1 | 88.4 |
| d,l-Glaucine . HBr | 100.8 | 93.3 | 91.4 |

After 12 months at 55° C. the phosphate salt had an assay of 101.8 percent and the hydrobromide an assay result of 87.3 percent.

EXAMPLE 6

In a procedure similar to that of Example 5, syrup formulations were prepared, placed in amber glass bottles and transparent (flint) glass bottles, and held under conditions of ambient temperature with continuous exposure to light. (About 2000 Foot-candles of combined fluorescent and incandescent light, for 24 hours/day.)

After one month, the d,l-glaucine hydrobromide assay of amber bottles was 84 percent, that of flint glass was 74.5 percent. D,l-glaucine phosphate in amber glass had an assay of 97.7 percent, in flint glass 90 percent. Codeine phosphate appeared stable in both types of container, with assays of 100 percent.

In similar operations, the crystalline glaucine phosphate (2.3) salt was found to retain over 98 percent of the original glaucine content after two months at 40° C.

EXAMPLE 7

The abuse potential of d,l-glaucine phosphate was studied in two monkeys in a procedure similar to that described by Deneau, et al., Psychopharmacologia 16(1):30-48, 1969.

In this procedure, the test monkeys are restrained and a catheter inserted into the external jugular vein for injection of test substances in response to pressing a bar lever by the monkey. The test monkeys are first habituated to self-administer codeine at a rate of 100 micrograms/kilogram per injection. The self-administration rate of the two monkeys so trained and habituated was about 100 to 150 lever pushes per two hour session at the 100 microgram codeine level. When d,l-glaucine phosphate (2:3) was substituted for codeine, the monkey response rate was found to decline, from 100-150 responses/two hour session for codeine to 10-20 responses/two hour session after substitution of d,l-glaucine phosphate, at rates of 50, 100, 200 and 400 micrograms per kilogram injection.

EXAMPLE 8

Physical dependency liability was evaluated in mice by the procedure of Saelens, et al., Arch. Int. Pharmacodynam, 190:213-218, 1971. In this procedure, mice are administered increasing doses of a test compound at intervals on two consecutive days. The last dosage on the second day is followed by intraperitoneal injection of the morphine antagonist, naloxone, at a dosage of 100 mg/kg, and the mice are observed for characteristic jumping behaviour indicative of opiate withdrawals or morphine antagonism. In these operations, morphine sulfate produced stimulation and Straub tail in mice, followed by jumping in 5 of 9 mice (96 jumps total) after naloxone treatment. Codeine phosphate produced Straub tail and stimulation, and naloxone induced jumping in 2 of 6 mice (23 jumps total). d,l-Glaucine phosphate (2:3) produced no Straub tail at the highest dose (100 mg/kg) and no jumping behaviour in any of the eight mice tested.

EXAMPLE 9

Several d,l-glaucine salts were prepared as 0.2 percent (weight by volume) solutions in distilled water. The various salt solutions were evaluated for palatability by touching a few drops to the tongue. In these operations, which included blind sampling by a trained flavor formulator experienced in flavoring of formulations containing agents such as codeine and dextromethorphan, the hydrobromide was characterized as objectionable with a bitter, sharp and metallic initial taste which increased with time. The sulfate, maleate, citrate, acetate and p-toluenesulfonate salts were similar to the hydrobromide and similarly objectionable. The salicylate and succinate salts were ranked as more objectionable than the hydrobromide. d,l-Glaucine phosphate (2:3) was found to lack the sharp, metallic flavor and to be unobjectionable.

EXAMPLE 10

A. A flavored cough syrup formulation is prepared to contain the following:

| Ingredient | Amount |
|---|---|
| Sucrose (100% Invert Sugar-Dry Basis) | 26.4 Grams |
| Sorbitol Syrup USP | 10 Milliliters (Ml) |
| Glycerine | 5 Ml |
| Alcohol USP | 5.4 Ml |
| Piperonal | 10.0 Milligrams (Mg) |
| Vanillin | 7.5 Mg |
| Ethyl Vanillin | 10.0 Mg |
| Ethyl Maltol | 7.5 Mg |
| 1-Menthol | 7.5 Mg |
| d,l-Glaucine Phosphate (2:3) | 600 Mg |
| Purified Water USP | q.s. to 100 Ml Total |

The syrup contains 0.6 percent (weight by volume) d,l-glaucine phosphate and a 5 ml dosage unit (1 teaspoon) contains 30 mg of active phosphate salt. The syrup can be sealed into 5 ml plastic lined foil pouches, or filled into conventional glass bottles. Dosage units of 15 mg and 20 mg per 5 ml dose can be made by using 300 or 400 mg of d,l-glaucine phosphate (2:3) or l-glaucine phosphate (2:3) or mixtures thereof in the above formula.

B. Tablets are prepared as follows: 40 grams l-glaucine phosphate; 150 grams of modified starch (Sta-Rex 1500) are mixed and granulated with sufficient aqueous alcohol (75 percent water, 25 percent ethanol) to prepare a granulation. The granulation is dried and mixed with 15 grams starch USP; 1.5 grams stearic acid (40 mesh); 0.5 grams hydrogenated vegetable oil (40 mesh) 3 grams colloidal silicon dioxide and microcrystalline cellulose q.s. to 300 grams. The ingredients are mixed and compressed into 300 milligram tablets using 11/32 inch tablet dies. The tablets contain 40 milligrams of l-glaucine phosphate each.

C. Capsules are prepared by blending 5 grams, d,l-glaucine phosphate, and 5 grams l-glaucine phoshate; 3 grams colloidal silica; 2 grams stearic acid and 285 grams lactose; and filling the blend into No. 2 gelatin capsules, 300 milligrams per capsule. This provides 10 milligrams of glaucine phosphate per capsule. Larger unit dosages, such as 15, 20 or 25 mg, can be prepared by using 15, 20 or 25 grams glaucine phosphate and lactose q.s. to 300 grams. Smaller dosages are similarly prepared.

D. Troches are prepared by mixing 30 grams d,l-glaucine phospate (2:3), 435 grams powdered sugar and 35 grams powdered acacia; adding sufficient water to form a pliable mass; rolling the mass into a cylindrical shape and dividing the mass into 0.5 gram segments.

EXAMPLE 11

In other operations, various dosages of d,l-glaucine phosphate (2:3) were administered to groups mice by the oral route or by intraperitoneal injection, and the dosage which is lethal to 50 percent of the mice ($LD_{50}$) was calculated from the mortality observations within 72 hours after administration. The $LD_{50}$ for intraperitoneal injection was found to be 178 mg/kg. The oral $LD_{50}$ in these operations was found to be equal to or greater than 681 mg/kg.

These data, together with the $ED_{50}$'s determined in Examples 2 and 3, indicate that the phosphate salt has a therapeutic ratio ($LD_{50}/ED_{50}$) of 38 for oral antitussive activity and 10 for intraperitoneal activity.

In other operations, l- and d-glaucine phosphate (2:3) were orally administered to separate guinea pigs and plasma concentrations of l- or d-glaucine were measured at intervals after dosing. These data showed that the l-glaucine phosphate produced high plasma levels of glaucine within 15 minutes after dosing, and that plasma levels remained high, generally 3 to 6 or more times as great as the plasma levels of d-glaucine, over a two hour test period.

EXAMPLE 12

Text compounds were evaluated for analgesic activity in the phenyl-p-quinone mouse writing test of Hendershot & Forsaith, J. Pharmacol. Exptl. Therap. 125(3) 237 (1959). The test compounds were administered orally 30 minutes prior to the phenyl-p-quinone challenge. In these operations, the oral $ED_{50}$'s for d-glaucine. HBr, codeine phosphate and d,l-glaucine phosphate (2:3) were found to be 34.0, 21.2 and 23.0 mg/kg respectively.

What is claimed is:

1. A phospate salt of a member of the group consisting of l-glaucine, d,l-glaucine and mixtures thereof.

2. Compound of claim 1 wherein the compound is l-glaucine phosphate.

3. Compound of claim 2 wherein the compound is l-glaucine phosphate having from about 1 to about 2 molar proportions of phosphoric acid per molar proportion of l-glaucine.

4. Compound of claim 2 wherein the compound corresponds to l-glaucine phosphate (2:3).

5. Compound of claim 1 wherein the compound is d,l-glaucine phosphate.

6. Compound of claim 5 wherein the compound is d,l-glaucine phosphate having from about 0.3 to about 0.7 molar proportions of phosphoric acid per molar proportion of glaucine.

7. Compound of claim 5 wherein the compound corresponds to d,l-glaucine phosphate (2:3).

8. A composition comprising from about 0.01 percent by weight to about 95 weight percent by weight of a phosphate salt of a member of the group consisting of l-glaucine, d,l-glaucine and a mixture thereof, in admixture with a pharmaceutical carrier.

9. Composition of claim 8 wherein the composition is in dosage unit form adapted for oral administration as an antitussive agent, and wherein the compound contains from about 0.1 to about 60 milligrams of the glaucine phosphate per unit.

10. Composition of claim 8 or 10 wherein the compound is phosphate salt of d,l-glaucine.

11. Composition of claim 8 or 10 wherein the compound is phosphate salt of l-glaucine.

12. Composition of claim 9 wherein the salt corresponds to the formula $C_{21}H_{25}NO_4 \cdot 1.4\text{-}1.6\ H_3PO_4$.

13. Composition of claim 8 wherein the composition is in the form of a solution of said phosphate salt in an aqueous cough syrup vehicle.

14. A method of alleviating coughing in animals, comprising orally administering to an animal an antitussive amount of a phosphate salt of a member of the group consisting of l-glaucine, d,l-glaucine and mixtures thereof.

15. Method of claim 14 wherein the compound is d,l-glaucine phosphate.

16. Method of claim 15 wherein the compound coresponds to d,l-glaucine phosphate (2:3).

17. Method of claim 14 wherein the compound is l-glaucine phosphate.

* * * * *

UNITED STATES PATENT AND TRADEMARK OFFICE
CERTIFICATE OF CORRECTION

PATENT NO. : 4,315,010
DATED : February 9, 1982
INVENTOR(S) : Samuel S. M. Wang

It is certified that error appears in the above-identified patent and that said Letters Patent are hereby corrected as shown below:

Column 2, line 23, "0.3 to 0.4" should read --0.3 or 0.4--.

Column 5, line 28, "separated" should read --separation--.

Column 5, line 47, "solution" should read --addition--.

Column 6, line 13, "242.0°" should read --242.9°--.

Column 7, line 58, "d,l-glaucine.1.5$H_3PO_3$" should read --d,l-glaucine.1.5$H_3PO_4$--.

Column 9, line 48, "(2.3)" should read --(2:3)--.

Column 12, line 5, "21.2" should read --21.1--.

Column 12, Claim 8, line 27, "95 weight percent" should read --95 percent--.

Column 12, Claim 10, line 36, "10" should read --9--.

Column 12, Claim 11, line 38, "10" should read --9--.

Signed and Sealed this

Twenty-ninth Day of June 1982

[SEAL]

Attest:

GERALD J. MOSSINGHOFF

Attesting Officer — Commissioner of Patents and Trademarks